United States Patent [19]

Collins et al.

[11] Patent Number: 4,565,669
[45] Date of Patent: Jan. 21, 1986

[54] MICROWAVE ASHING APPARATUS

[75] Inventors: Michael J. Collins; Wyatt P. Hargett, Jr., both of Matthews, N.C.

[73] Assignee: CEM Corporation, Matthews, N.C.

[21] Appl. No.: 487,307

[22] Filed: Apr. 21, 1983

[51] Int. Cl.[4] .................... G01N 31/12; H05B 6/64
[52] U.S. Cl. ............................ 422/78; 219/10.55 R; 219/10.55 E; 219/10.55 M; 436/155
[58] Field of Search ............ 219/10.55 R, 10.55 E, 219/10.55 M; 422/78; 436/155, 159, 160, 908

[56] References Cited

U.S. PATENT DOCUMENTS

| | | | |
|---|---|---|---|
| 1,743,035 | 1/1930 | Halvorson | 436/155 |
| 2,688,532 | 9/1954 | Jill | 436/908 X |
| 3,591,751 | 7/1971 | Goltsos | 219/10.55 E |
| 3,654,417 | 4/1972 | Javes et al. | 219/10.55 R |
| 3,783,220 | 1/1974 | Janizaki | 219/10.55 E |
| 3,941,967 | 3/1976 | Sumi et al. | 219/10.55 E |
| 4,080,168 | 3/1978 | Abu-Samra et al. | 422/68 X |
| 4,307,277 | 12/1981 | Maeda et al. | 219/10.55 R |
| 4,347,216 | 8/1982 | Kawasaki et al. | 422/78 |

FOREIGN PATENT DOCUMENTS 0091436  7/1981  Japan .................... 219/10.55 M

*Primary Examiner*—Barry S. Richman
*Assistant Examiner*—Robert J. Hill, Jr.
*Attorney, Agent, or Firm*—Raymond F. Kramer

[57] ABSTRACT

An apparatus for ashing materials which comprises a chamber, a source of microwave radiation for direction onto contents of the chamber, and in the chamber a support, such as a fused quartz pad or crucible, for the material to be ashed, and an ashing means of a stable microwave absorptive material, capable of being heated to high temperature by microwave radiation, such as a flat block of silicon carbide or a plurality of such blocks with openings therein to accommodate the crucible. The ashing means is in contact with the support for the material to be ashed and is capable of heating such support and such material to an ashing temperature. When a fused quartz fiber pad, preferably of the nonwoven cloth type, is employed on top of and in contact with the ashing means of microwave absorptive material, as a support for the material to be ashed, it is preferred to cover such material with another such pad, which inhibits loss of the ash due to its being carried out of the chamber, as by an exhaust fan, while yet permitting the release of gases generated during the ashing process. Also disclosed are processes for ashing materials and for analyzing such materials for ash content, which processes may be practiced with the aid of the described apparatus.

2 Claims, 3 Drawing Figures

MICROWAVE ASHING APPARATUS

This invention relates to apparatuses and processes for ashing an ashable material and for determining the ash content of such material. More particularly, the invention relates to such apparatuses and processes which utilize microwave radiation and a microwave absorbing material capable of being heated to an ashing temperature, which are employed in conjunction with a temperature stable support for the material to be ashed, which support is in contact with the microwave absorptive material and transmits the heat generated therein to the ashable material.

Analyses for ash contents of various materials are standard laboratory procedures. Such analyses may be effected to ascertain the nature of certain products or to determine the qualities thereof. Often such analyses will be used to determine whether manufactured goods meet standards. For example, when inert mineral fillers are employed in synthetic organic polymeric materials, such as "plastics" it will often be desirable to analyze the filled product for ash content, which will be indicative of the inorganic filler content, because variations in filler content may alter the properties of the product and take it out of specification limits. Ashing may also be effected when it is desired to prepare a sample for further analysis of its inorganic components, as when radioactive materials are being analyzed. Normally such ashings are carried out by heating of specimens or samples in a high temperature oven or a furnace, which often takes an hour or more.

Microwave heatings of relatively small quantities of various materials to effect drying, evaporation, chemical reaction and digestion, and for other laboratory and analytical purposes have been suggested in various patents, and microwave apparatuses and systems for performing such operations have been marketed. Among such apparatuses are the AVC TM -80 Moisture/Solids Analyzer, the AVC TM MP Automatic Volatility Computer and the MDS TM 81 Microwave Drying/Digestion System, all of which are manufactured and sold by CEM Corporation. In U.S. patent application Ser. No. 450,198 (Collins and Hargett, Jr.) incorporated herein by reference, the use of such apparatuses in conjunction with microwave absorbing material for thermally heating a sample to be analyzed is described.

Although microwave apparatuses have been employed in conjunction with microwave absorbing materials to analyze samples for contents of moisture and other volatiles, to digest various materials and to promote chemical reactions, applicants do not know of any prior art which discloses or suggests the employment of microwave apparatuses for ashing materials or in analytical procedures for determining the ash contents of samples. The apparatuses and procedures of this invention, as described in the specification and as claimed, are considered to be novel and unobvious from the prior art.

In accordance with the present invention an apparatus for ashing an ashable material comprises a chamber, a source of microwave radiation for radiating onto contents of such chamber, a stable, essentially non-oxidizable support for material to be ashed and an ashing means of a stable, essentially non-oxidizable microwave absorptive material capable of being heated by microwave radiation to a temperature in the range of 400 to 1,000° C. without deterioration, which is in contact with the support and is capable of heating it and the material to be ashed to such an ashing temperature. The best material known for the ashing means is silicon carbide in flat or other non-particulate solid form and preferred supports are pads of fused quartz fibers, or crucibles of quartz or suitable high temperature resistant material. The invention also relates to processes for ashing materials and for analyzing samples of materials for their ash contents. In a preferred form of the apparatus aspect of the invention, an apparatus for ash analysis of an ashable material selected from the group consisting of synthetic organic polymers, waste water sludges, activated sludges, industrial wastes, river bottom sediments, lake bottom sediments, stream bottom sediments, coals, foods, papers and structural materials, while removing gaseous products of combustion from the material during ashing without removing any ash, said apparatus comprises means defining a chamber, a source of microwave radiation for radiating onto contents of said chamber, a substantially flat silicon carbide ashing means located within the chamber, which is stable and essentially non-oxidizable, capable of being heated by microwave radiation to a temperature in the range of 400° to 1,000° C. without deterioration, and which has horizontal flat top and bottom surfaces, and first and second thin flat non-woven cloth pads of fused quartz fibers both of which pads have flat upper and lower surfaces, the first of which pads is located on top of and in continuous intimate contact with the top surface of the silicon carbide ashing means, and the second of which pads is located atop the first pad, so that ashable material to be analyzed for ash content may be placed between such pads for such ashing to be effected, said second pad being permeable to passage of gas released during ashing of the ashable material.

BRIEF DESCRIPTION OF DRAWINGS

The invention will be readily understood from the present specification and the following description of preferred embodiments thereof, taken in conjunction with the drawing, in which:

In FIG. 1 microwave apparatus 11 includes internal walls like that represented by numeral 13, a bottom 15 and a door 17, defining a chamber 19, in which there are positioned insulating means 21 in the form of a chair-shaped stand, ashing means 23, support 25 and ashable material 27.

Figure 1:
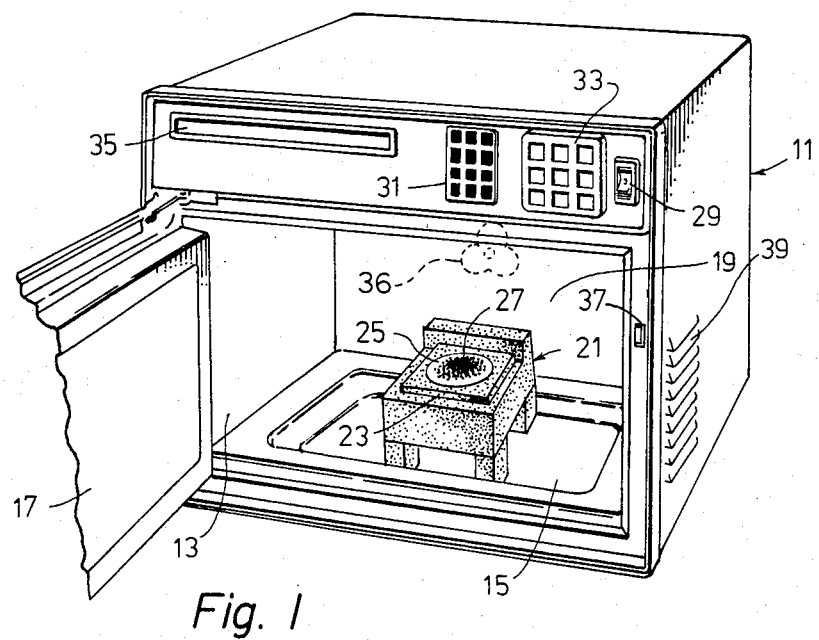
FIG. 1 is a perspective front view of an apparatus of this invention, useful for ashing samples of ashable materials.

The microwave apparatus, utilized to direct microwave radiation onto the ashing means and the material to be ashed, may be like that marketed as their MDS-81 Microwave Drying/Digestion System by CEM Corporation, and described in their bulletin entitled CEM Corporation Microwave Drying/Digestion System MDS-81 (Laboratory Microwave System), published in 1981, or other suitable magnetron or equivalent microwave generators may be employed. Such may preferably generate focussed microwave radiation, concentrated or directed at the ashing means, but in some instances it may be desirable to employ a mode stirrer to disperse the microwave radiation although such is not necessary because the ashing means preferably silicon carbide in non-particulate solid form, will absorb all of the microwave energy radiated. The illustrated preferred microwave apparatus (like that of the MDS-81 system) includes an on-off switch 29, a programmable microprocessor digital computer (not shown) capable of programming a plurality of microwave radiation powers that can be applied over a plurality of sequential time periods (or only one), controls 31 and 33 for such microprocessor, a read-out screen 35, an exhaust fan, 36, which is preferably of controllably variable speed, and a door latch 37. Although the exhaust fan is not seen, it is shown in the drawing, being within the walls of the apparatus and inlets 39 for air flow are illustrated. Similar inlets are present on the other side of the apparatus and communicate with the fan which exhausts air through outlets at the rear of the apparatus or through a single outlet which may be communicated with an exhaust tube, which may be connected to an appropriate exhaust system, such as a fume hood, which may further communicate with a scrubber and/or with the outside air.

Figure 2:
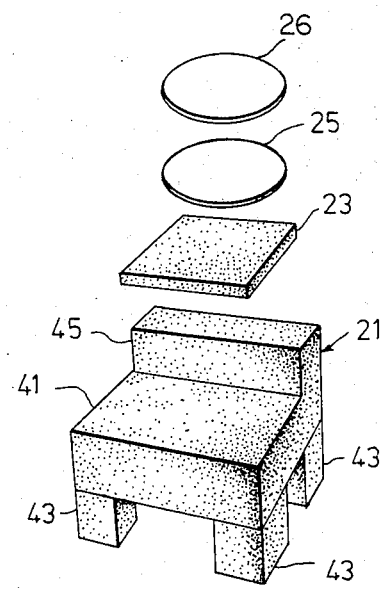
FIG. 2 is a perspective view, with parts thereof separated for clarity, of a support for the material to be ashed, an ashing means, a cover for the material to be ashed, and an insulating stand, like those illustrated in FIG. 1.

In FIG. 2 chair-shaped insulating means 21 is comprised of an L-shaped upper part 41 and legs 43, all or part of which may be integrated into a single unit. Normally the insulating material, which inhibits loss of heat from ashing means 23 through the lower surface thereof, is made of a refractory material, such as fire brick or similar high temperature stable insulator. The upper portion 45 of L-shaped part 41 serves as a backing member, to facilitate removal of support 25 and any material 27 which is to be ashed, when a spatula or other removal device is inserted between support 25 and ashing means 23. It also serves as an insulator, to prevent a loss of heat through the back side of the ashing means. Although they are not illustrated in the present drawing it is also within the invention to have refractory material edging strips or equivalents about the other sides of the ashing means.

Figure 3:
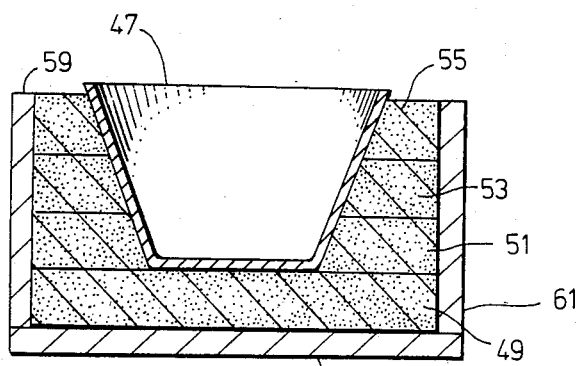
FIG. 3 is a sectional elevational view of a support in the form of a crucible set in insulated ashing means shaped to conform to the crucible.

In FIG. 3 a plurality of blocks of microwave absorbing material (silicon carbide) is illustrated, fitted together to form ashing means for surrounding a crucible 47. Crucible 47 rests on flat bottom block 49, which has no opening in it, and flat blocks 51, 53 and 55, placed atop bottom block 49, are so shaped as to form an opening into which the crucible may be placed, with its sides contacting such blocks where they define the opening for the crucible. As illustrated, the openings in the three upper ashing blocks are tapered so as to fit the contour of the crucible but in some instances it may be preferable, to facilitate manufacture of the blocks, to have them drilled, creating circular untapered openings, only portions of which will contact the crucible. While such construction will be less efficient in heating the crucible it will be adequate in many instances. About the ashing means are located a bottom 57 and sides 59 and 61 of refractory material to promote energy conservation and to facilitate rapid heating of the crucible and its contents, and the maintenance of high temperatures therein.

The apparatus for the application of the microwave energy for a sample of material to be ashed may be any such suitable microwave apparatus that can direct microwave radiation onto the material to be ashed. Household microwave ovens are not usually satisfactory but they may be useful in some instances. Preferably, the apparatus will incorporate a microprocessor, digital computer and controls for regulating the application of microwave radiation to the material to be treated. Thus, the microwave radiation may be applied for desired lengths of time and different levels of radiation may be applied, if desired. It is also preferred for the microwave apparatus to include read-out means, especially for automatic analyzers, which continuously can weigh the sample or the sample plus tare so that the progress of the analysis may be followed. In other cases temperatures applied and treatment conditions may be monitored by reference to such a read-out screen.

Preferred microwave apparatuses which may serve as the basic apparatus structure, to be completed by additions of support, pad and material to be treated, are the AVC Automatic Volatility Computer (preferably AVC-MP), the AVC-80 Moisture/Solids Analyzer and the MDS-81 Microwave Drying/Digestion System, all of which are made by CEM Corporation. Of these the MDS-81 is most preferred. The various apparatuses are described in operation and service manuals entitled Automatic Volatility Computer AVC TM, and Automatic Volatility Computer Model AVC TM MP, published in 1975 and 1979, respectively, by CEM Corporation, and in an article entitled Moisture/Solids Control Using a New Analytical Technique, by the present inventor, published in American Dairy Review, May, 1979; in a brochure entitled CEM Corporation Moisture/Solids Analyzer, AVC-80, published in 1981; and in a brochure entitled CEM Corporation Microwave Drying/Digestion System, MDS-81, Laboratory Microwave System, published in 1981. These CEM Corporation publications, all of which are incorporated herein by reference, contain specifications for such equipment. The various apparatuses all include exhaust means, e.g., fans and inlets and outlets, to permit removal of products of combustion and to supply air to the system. In addition to the publications mentioned, the mentioned apparatuses are described in U.S. Pat. Nos. 3,909,598 and 4,291,775, and in U.S. patent applications Ser. Nos. 21,986 for Analytical Method and Apparatus; 29,882 for Method and Apparatus for Improving Weighing Accuracy (Collins et al.); Ser. No. 603,354 for Automatic Volatility Computer; and Ser. No. 416,011, for Analytical Microwave Oven (Collins and Manchester), all of which are also incorporated herein by reference.

It is noted that in the apparatuses mentioned the microwave power range is from 0 to 100% of full power (600 watts in most instances) in 1% increments. Of course, lesser and greater powers may also be employed, for example up to several kilowatts, e.g., 0.3 to 5 or 0.4 to 1 kw., but are usually unnecessary. In the United States the frequency of microwave radiation employed will normally be 2.45 gigahertz, and in Great Britain it is 0.896 gigahertz. However, such frequency can be in the ranges from 0.3 to 50 gigahertz (or higher), preferably being in the range of 0.8 to 3 gigahertz. The read-outs of the described apparatuses have as many as 40 characters in their alphanumeric displays and in some instances may include audible tones for operator feedback. The operator controls include a keyboard of up to 21 keys for input. In the case of such units incorporating electronic balances the sensitivities are approximately one part in 40,000 over a range of 5 grams to 100 grams.

One of the advantages of the present invention is that the described microwave apparatuses may be employed for ashing or in other analytical operations for which each apparatus may have been primarily designed, such as moisture determinations, volatiles analyses, fat content analyses, and for the promotion of chemical reactions. Usually when the apparatuses are employed for ashings of materials they will be used at their highest power supply condition, which is often about 600 watts for the commercial microwave apparatuses mentioned.

The ashing means is of a microwave absorptive material which does not have a Curie temperature below desired ashing temperatures and which is capable of being heated by microwave radiation to a temperature in the range of 400° to 1,000° C. Sometimes the ashing range can be even higher, being limited by the melting, sublimation or decomposition points of the equipment materials being employed or of the ashable substance or its oxide(s). In some instances, temperatures as high as 2,000° C. are attainable but normally the range of 400 to 1,000° C. is adequate and sometimes a range of 400° or 600° to 800° C. is more preferred. The ashing means is one which is stable at the intended use temperatures and is essentially or completely non-oxidizable at such a temperature. It should also be structurally sound at such use temperatures, being resistant to disintegration, cracking and powdering. Although various materials are capable of absorbing microwave radiation and of being heated to temperatures in the ranges described, silicon carbide is the most useful and most preferred of such materials. Silicon carbide in powder, granular or other small particulate form (wherein the effective diameters of the particles are usually up to 0.5 or 1 cm.) can be heated by microwave radiation but generally in such a form it is not sufficiently effective to be employed as an ashing means for a variety of ashable materials such as may be encountered and for the analyses of which the present apparatus is intended. However, silicon carbide which is in continuous or non-particulate solid form is very satisfactory and has been employed successfully in test analyses of various materials for ash contents.

The continuous silicon carbide solid ashing means may be in various shapes or forms to suitably accommodate a support, which is very preferably employed between it and the sample of ashable material intended for ashing. Thus, especially when the support is a flat pad, deposit, cloth or paper of high temperature resistant material the ashing means will preferably be in flat block form. Such a block may be a flat prism and preferably is a regular prism, such as a square prism, and is of a thickness in the range of 0.3 to 2 cm., preferably 0.5 to 1.5 cm., e.g., about 0.9 cm., with a side dimension (for the square) in the range of 5 to 10 cm., preferably 6.5 to 8.5 cm., e.g., about 7.6 cm. Suitable materials may be commercial "finishing sticks", which may be used to true grinding wheels; of these those sold by Norton Co. as JKV finishing sticks are preferred, but other bonded silicon carbide products may also be employed. Among these are Norton Company's Cryston silicon nitride bonded silicon carbide, designated CN 137 and CN 233. Even if such products may physically deteriorate after many uses they are not expensive, so scheduled periodic replacements, such as after every 100 to 10,000, or 1,000 to 5,000 analyses may be desirable.

When the support is a crucible or walled container the silicon carbide ashing means may be shaped to fit around the crucible. It may be in a single piece or, to facilitate manufacture, may be made from several slabs or blocks of the microwave absorptive material, each having a suitable shape (usually openings) to conform to the crucible or container. In such cases a bottom block will usually support the container and a plurality of other flat blocks with central openings will conform to the shape of the crucible sides, either exactly or approximately (approximately when holes are drilled through the absorptive blocks) to promote heat transfer to the crucible. Although for best operation of the present apparatus a supporting means for the specimen to be ashed will be present (the use of which allows easier weighings of the sample before and after ashing, and prevents contamination of the ashing means), it is within the invention to have the ashable material in direct contact with the ashing means. In some instances a crucible or other container may be made of the material of the ashing means or such ashing means may be in the form of a thin flat heating support (comparatively light in weight to facilitate weighings of it and the ashable material before and after ashing) and may be in contact with a larger block of microwave absorbent material which is capable of supplying more heat to the specimen to be ashed.

The support for the ashable material, which is usually either a thin flat pad-like material or a container, such as a crucible, previously mentioned, is of a stable, essentially non-oxidizable material which can resist deterioration and oxidation at ashing temperatures. While other supports may be employed, for analyses of products for ash contents it is highly preferable to utilize a thin pad, usually in disc form, of fused quartz fibers. Such a pad is non-woven and is made from fibers of fused quartz, although in some circumstances it may be possible to utilize glass fibers too, especially those of quartz glass. Such pads are preferably of a thickness in the range of 0.06 to 2 mm., more preferably 0.08 to 0.2 mm., e.g., about 0.1 mm. and have a major single surface area in the range of 15 to 30 sq. cm., more preferably 20 to 25 sq. cm., e.g., 23 sq. cm., and when circular will preferably be of a diameter of about 5.4 cm. Suitable such supports are those sold as Wattman 5 quartz glass or quartz microfiber pads, designated QM-A. The covers, such as that identified by numeral 26, are preferably of the same material sizes and properties as the support (identified as numeral 25)

When a container or crucible is utilized as a support, which is preferable when the ash resulting is to be analyzed further, it is preferred that silica or quartz crucibles be employed, such as Vycor ® crucibles, e.g., Vycor Brand Glass No. 7,900, but porcelain, other glasses, ceramics and refractories, sometimes only at lower ashing temperatures, may be employed. Of course, the crucible wall thickness should be as thin as feasible, usually being less than 2 mm. and preferably being about 1 mm. The thinner the material of the container or the pad support the less heat it will hold after removal from the microwave apparatus chamber and therefore the sooner the ashed material may be weighed for analytical purposes, without any special cooling procedures being necessary. Of course, the light weight pad of quartz fibers, which often may weigh only from 50 mg. to 1 g., preferably 100 to 400 mg., and which is of relatively little heat capacity, is preferred for such quick weighings after completion of ashing.

The materials to be ashed, using the present apparatus and process, may be any of a wide variety of substances containing components which are stable at ashing temperatures or which form stable compounds at such temperatures (usually oxides). Commercially, ash analyses of synthetic organic polymeric plastic materials, coals, sewage plant sludge, foods, structural materials and papers may be more important, but ash analyses of many other materials may also be of significance.

The insulating material that may be employed to help to prevent heat loss from the ashing means (except to the support and the material to be ashed) may be any suitable insulation which is stable under the conditions of the ashing operation. Like the support material, normally it will not be microwave absorbent and will not be heated by the microwave radiation. The insulation may be in various forms but preferably will be shaped so as to prevent contact of the ashing means with the interior (bottom) of the microwave apparatus chamber, which is normally of a metal. Among the insulating materials which may be employed refractories are preferred, preferably in suitable form, such as cut from firebrick. Among such materials may be mentioned aluminum silicates, silica, alumina, mullite, magnesite, dolomite, forsterite and zirconia. Specific preferred refractories or other insulators will be employed depending on the temperature to which they are to be subjected. The insulation, which will at least partially insulate the ashing means so as to inhibit heat loss therefrom except to the support and the material to be ashed, will normally support the ashing means and insulate it from the chamber floor, thus preventing heat loss from a major surface of the ashing means, but it may also be utilized to insulate sides and even a portion of the top of the ashing means, when desirable.

In the process aspect of this invention an ashable material is ashed by applying microwave radiation to it and to an ashing means capable of being heated by such radiation to a temperature in the ashing range, 400° to 1,000° C. Such process may be effected without pre-heating of the ashable material, although pre-heating is preferred in many instances to further speed the ashing operation.

Because one of the important advantages of the present invention is the speed of the ashing process, which enables the invention to be employed for control analyses during the productions of various substances, the ashing process will usually last no more than 20 minutes and sometimes may be as short as 30 seconds. Normally it will take from 1 to 10 minutes, frequently from 2 to 7 minutes and often preferably from about 3 to 5 minutes, for complete ashing of the sample to be effected. Various weights of samples to be ashed may be utilized, often in the range of 0.1 to 50 grams but normally such weight will be from 1 to 10 grams and usually it preferably will be from 2 to 5 grams. The sample may initially contain volatile materials, such as moisture, or it may be anhydrous.

When the rapid microwave ashing procedure of this invention is practiced without preheating of the sample the sample is placed on a suitable support, either a pad, crucible or other support, preferably of quartz, and after appropriate weighing, is placed atop, inside, or in other desired relationship with the ashing means, the microwave apparatus is closed, and application of microwave radiation to the ashing means (and the sample) is begun. The quartz pad isn't objectionably insulating and does not prevent the supported sample from quickly being raised to an ashing temperature by the heat generated by the ashing means. It also allows quick cooling of it and the ashed material after removal from the microwave apparatus. The ashing means will be insulated from contact with the metal bottom of the microwave apparatus, preferably by a refractory material, and such material will be of a suitable shape, such as was previously described in the specification and shown in the drawing. To conserve energy and promote faster heating of the ashing means the sides and a portion of the top of the ashing means may be insulated by the refractory material, if desired.

The ashing means will usually soon glow red, often within about 3 or 4 minutes, indicating that it is at a temperature of about 600° to 800° C., which temperature is usually sufficient to effect the desired ashing. Of course, utilization of more power, a larger ashing block and more insulation will allow the temperature to be increased further in such time or will allow such temperature to be attained in a shorter period of time. While the microwave energy is being applied controlled gas circulation is maintained, preferably by means of a variable speed fan responsive to automatic controls in the apparatus, and the circulating air provides oxygen for the ashing and removes gaseous combustion products. For materials of generally known composition and ashing behaviors the application of microwave energy and the operation of the fan may be automatically controlled so as to terminate after completion of the ashing, although in some instances the fan may continue for a short period, e.g., a minute or so, after cessation of microwaving.

After completion of the application of microwave energy and of the ashing of the sample the support plus sample are removed from the microwave apparatus and, without special cooling, may be almost immediately (usually within a minute or two) weighed. Because prior to the ashing the weight of the support was known or was determined the percentage of ash in the product can readily be calculated, and this may often be done automatically by the automatic microwaving apparatus employed. In instances when the ashed material is being prepared for further analysis it will normally be preferred to employ a crucible or other suitable container, rather than a quartz fiber pad because of some difficulty encountered in completely removing the ashed material from the pad and because of the possibility of some contamination of the sample with the pad material. In such cases quartz crucibles of the type previously described are highly preferable.

In some instances, particularly with certain types of powders and pellets, a small retaining collar of suitable material (it does not have to be heat-resistant) may be employed to prevent the sample from flowing or rolling off the pad. To use such a collar, first the sample pad is tare weighed, the collar is placed on the pad and the sample is added inside the collar, after which the collar is removed and the weight of the pad plus sample is taken in the usual manner. Then the collar is replaced before transferring the sample to the ashing block, and after such transfer has been effected it is removed and ashing is commenced. It is not usually necessary to replace the collar after conclusion of ashing but sometimes this may also be desirable.

Automatic weighing devices in the microwaving apparatuses described may be employed for weighings before and after ashing, or such devices can be removed from the apparatuses or their use can be omitted. If used, transfers of materials to external balances may be saved and often automatic determinations of ash contents can be obtained more easily. Of course, if a built-in balance is to be employed it will usually be desirable to minimize weights of the ashing means, support and insulation.

To further speed the ashing process and improve its use as a control mechanism for various processes the ashing means may be pre-heated to a red heat or other suitable elevated temperature and the support plus sample may be placed on it, with the microwave radiation being continued during the ashing process so as to maintain or elevate the temperature of the ashing means. Thus, by following this method, one may speed up the ashing process by the time it normally would take to heat the ashing means to ashing temperature, which will result in improved applicability of the ash analysis method to quality control or regulation of operations that produce the ashable material.

The apparatuses and processes of this invention are much superior to those normally employed for ashing materials for analytical purposes. The methods are accurate, as has been shown by test analyses in which results were compared with the "standard" results obtained by conventional ashing analyses. Yet, while accurate, the present method is much faster than methods of the prior art. For example, whereas complete ashing of a sample may be effected by the present method in 3 to 5 minutes, on the average, such may take from one to two hours in a muffle furnace or an ashing oven and further time may have to be allowed in the conventional ashing processes for cooling down of the material in its ashing container. Thus, conventional ashing techniques do not lend themselves to active control of manufacturing processes because by the time the results are known over an hour's production will have been completed. On the other hand, the microwave apparatus of this invention is readily portable and may be installed at the production site so that within about 10 minutes, allowing for weighings of the sample, the ash content of the product is known and the conditions of manufacture may be modified accordingly, if desirable.

In addition to the quick control that is possible by employing the present invention significant energy savings are made because furnaces and ovens normally take longer times to heat up and therefore must be kept hot so as to be ready for use. When such furnaces are gas fired special utility lines are needed, and there is the possibility of some contamination of the sample by the products of combustion. Also, such high temperature ovens may affect the temperature of the environment and can be hazardous to an operator, especially when he has to open the oven door for the insertion or removal of an ashable sample. Any noxious fumes given off by the ashable material during the ashing process are removed from the microwave apparatus by the exhaust system but often it is not feasible to employ exhaust systems with conventional furnaces because of the loss of heat involved (since the heat is conveyed to the ashable sample by such gases).

The following examples illustrate but do not limit the invention. Unless otherwise indicated all temperatures are in °C. and all parts are by weight.

EXAMPLE 1

A laboratory microwave system, MDS-81, manufactured and sold by CEM Corporation is employed as a source of microwave radiation for the ashing operation of this example. This apparatus includes a metal walled chamber measuring 38.1 cm. wide, 31.7 cm. deep and 19.1 cm. high, a keyboard with fifteen keys to enter data and run samples, and a readout which is 20-digit alphanumeric display, with an audible tone for operator feedback. The optional MDS-81 turntable is not utilized. The microwave power range is controllable, in 1% increments up to 600 watts, and the power applied is programmable in three individual time stages. A timer is incorporated in the apparatus which can be regulated by the second up to over 100 hours. The apparatus employs AC current of 60/50 Hz, and 115/220 volts, with 15 amperes being the maximum current flowing at 115 volts. Such apparatus is illustrated in FIG. 1 of the present drawing, which shows a recessed metal bottom on which a stand of refractory material rests, which holds an ashing means (from a Norton JKV finishing stick), a support pad (Wattman quartz glass) and a sample of ashable material to be processed. The apparatus also includes a variable speed exhaust fan for air circulation and for removal of any noxious gases which may be produced during ashing.

Nylon pellets, made by Allied Corporation, and containing various quantities of inorganic fillers, are analyzed for ash contents, using the described apparatus. By standard furnace ashing, utilizing a muffle furnace and a crucible, with desiccator cooling, which process takes over an hour, three different sets of pellets analyze as containing 39.78%, 32.74% and 0.36% of ash, respectively. Utilizing the present invention, as will be described, and averaging four runs for each type of nylon, such percentages average to be 39.59%, 32.33% and 0.29%, respectively, and standard deviations from the average are small, being less than 0.1%.

The insulating refractory stand for the ashing means is made of fire brick and is shaped like that illustrated in FIGS. 1 and 2. The ashing means is a flat square ashing block measuring 1.13 cm. thick by 7.6 cm. on each side and weighs 100 grams. The density of the block is less than that of absolutely solid or single crystal silicon carbide and the block is porous, which is considered to be desirable to preserve its structural integrity, facilitate ashing and prevent undue strains and cracking of the block upon heating. However, the block is what can properly be referred to as a continuous solid. The support employed is a non-woven fused quartz filter paper type material, circular in shape and of a diameter of 5.4 cm. and a thickness of about 0.13 mm., which weighs about 200 milligrams. The pad is porous and readily conducts heat from the ashing means to the sample being ashed. Optionally, there may be employed an air shield, to be disposed about the sample being ashed to prevent any light ashes from being "floated" off the support during the ashing process, a sample retaining collar to assist in holding the sample on the support during transfers, and a protective covering for the bottom of the chamber. However, none of these is necessary with respect to the present experiment and none was employed.

The ashing block, on the refractory support for it, is pre-heated three minutes at 100% power, at which point it glows red. The exhaust fan is set at moderate air flow, which will not disturb the sample being ashed. Using a top loading balance accurate to one milligram or to 0.1 mg., a sample pad is weighed and the reading is "zeroed" by pressing the "tare" button on the balance. If no tare feature is included with the balance the pad weight will be carried through the calculations in the normal way. Then the appropriate weight of sample (usually from 2 to 5 grams) is placed on the sample pad and the weight thereof is recorded. Using a spatula, the sample pad, with the sample thereon, is transferred to the ashing block, the door of the MDS apparatus is closed and the timer thereof is set for an appropriate time, usually from 2 or 3 to 5 minutes. At the completion of the ashing cycle a spatula is used to transfer the sample and pad from the ashing block to the balance. No special cooling is applied and no desiccator is used but about a minute may be allowed for the sample weight to stabilize on the balance. The final weight reading is taken and the percentage of ash in the sample is calculated, being equal to the final weight of the ash divided by the initial weight of the sample, with the ratio resulting being multiplied by 100. The ashing operation, after the three minutes preheating of the ashing block, takes another four minutes, during which time the temperatures of the sample pad and of the sample are raised to about 700° C., and the sample is completely ashed. During such time any noxious gases produced during combustion of the ashable sample are removed by the exhaust means of the microwave apparatus. It is found that the ashable material is not removed from the support pad to an objectionable extent during initial flaming or during the subsequent ashing, so that the results, which are obtained within less than ten minutes after introduction of the sample into the microwave apparatus, are accurate. Even if the readings are different (usually lower) than expected from standard furnace ashing procedures they are reproducible for particular samples and thereby can be equated to results obtained by such standard tests, which take more than an hour.

If loss of test material is a problem in any specific case this can be rectified by employing another pad like the support pad, on top of the specimen being ashed, to prevent any "fly-off" of such specimen. It is found that with the porous pad on top of the sample complete ashing still results, although in some cases it may be desirable to lengthen the ashing period by from one to five minutes.

The following table gives ashing results for the nylon pellet samples, A, B, and C, the runs for which are designated by a combination of sample and run numbers. The ashing time was 2½ minutes with the microwave power at 100% (600 watts) and the fan at moderate speed.

TABLE 1

| Run | Sample Initial Weight | Sample Final Weight | % Ash |
| --- | --- | --- | --- |
| A1 | 1.710 | 0.678 | 39.65 |
| A2 | 1.433 | 0.566 | 39.50 |
| A3 | 1.824 | 0.722 | 39.58 |
| A4 | 1.897 | 0.752 | 39.64 |
| B1 | 2.023 | 0.655 | 32.38 |
| B2 | 1.924 | 0.620 | 32.22 |
| B3 | 1.900 | 0.614 | 32.31 |
| B4 | 2.052 | 0.665 | 32.41 |
| C1 | 2.997 | 0.009 | 0.30 |
| C2 | 3.144 | 0.009 | 0.29 |
| C3 | 3.060 | 0.009 | 0.29 |
| C4 | 2.981 | 0.008 | 0.27 |

From the above results it is seen that the present apparatuses and processes are sufficiently accurate to be useful for ash analyses and for process controls over sample ash content ranges from as low as about 0.1% to about 50% or more, e.g., 0.3 to 40%. Results like those given above are also obtainable when instead of employing the single support pad described, another such support is in place above the specimens to be ashed and the ashing time is increased from 2½ minutes after placement of the preheated ashing block, to 7 minutes. Similarly, such results are obtainable when instead of employing an ashing pad of the type described, an ashing container such as a Vycor quartz crucible of the type described in the specification is utilized. However, in the case of the crucible the ashing means and refractory insulation will be modified to be like that shown in FIG. 3 and the ashing period will be extended to five minutes. Also, a short cooling period, e.g., 10 minutes, in a desiccator will be desirable to stabilize the weight of the container plus the resulting ash.

From this experiment it is evident that rapid ashing apparatuses and processes are provided by this invention which are employable as excellent analytical means and operations and which allow process control to be effected quickly and easily. Thus, when the apparatus is installed at the end of an extruder or pelletizer for filled or unfilled nylon, production specimens may be analyzed within ten minutes or less of their manufacture, so that any deviations from desired filler (or ash) content may be corrected quickly.

EXAMPLE 2

Instead of testing plastic pellets for ash content, as reported in Example 1, waste water sludge is ashed so as to permit the determination of total volatiles content thereof. The procedure followed is that of Example 1 with the exceptions that the sample size is in the range of 2 to 3 grams, averaging about 2.5 grams, the ashing time (the time in which the sample is subjected to heating, by a preheated ashing block), is from 4 to 5 minutes, averaging 4.5 minutes, three specimens are ashed and two quartz pads are used in each determination, one as the support for the specimen and the other as a cover for it. Also, the microwave radiation is controlled so that the sample is ashed at a temperature in the range of 500° to 600° C., ideally being about 550° C.

As a result of the microwave ashing analysis the percentages of volatiles (percentages of materials removed during ashing) are found to be 56.0%, 56.1% and 56.0%, respectively. The material tested is waste water sludge but in the same manner activated sludge, industrial wastes and river, lake, or stream bottom sediments may be ashed. In instances when pads are replaced by crucibles or other containers, such as described in Example 1 and shown in FIG. 3, essentially the same results are obtained. The speed of testing, which will usually be less than ten minutes, allows more tests to be performed in a given time period than is possible for the standard furnace ashing procedure, and thus allows more accurate averaging of the results because samples can be taken from various locations in a sludge tank. Also, the microwave apparatus and balance, being readily portable, may be employed at the sites of the sludge tanks, saving the transportation of specimens to central laboratories with resulting delays, and facilitating control of any treating processes that produce the sludges.

EXAMPLE 3

The experiments of the previous examples are also repeatable without initial pre-heating of the ashing block. In such experiments, which take additional time, due to the need to heat the block to ashing temperature, any moisture or other microwave-volatilizable material may be driven off by the microwave radiation while the ashing block is being heated by additional such radiation. An additional 3 to 5 minutes, e.g., 4 minutes, are allowed for heating the ashing block to ashing temperature. Otherwise, the experiments reported in Examples 1 and 2 may be repeated and essentially the same results are obtainable.

The invention has been described with respect to various illustrations of preferred embodiments thereof but it is not to be limited to these because it is evident that one of skill in the art, with the present specification before him, will be able utilize substitutes and equivalents without departing from the invention.

What is claimed is:

1. An apparatus for ash analysis of an ashable material selected from the group consisting of synthetic organic polymers, waste water sludges, activated sludges, industrial wastes, river bottom sediments, lake bottom sediments, stream bottom sediments, coals, foods, papers and structural materials, while removing gaseous products of combustion from the material during ashing without removing any ash, said apparatus comprising means defining a chamber, a source of microwave radiation for radiating onto contents of said chamber, a substantially flat, silicon carbide ashing means located within the chamber, which is stable and essentially non-oxidizable, capable of being heated by microwave radiation to a temperature in the range of 400° to 1,000° C. without deterioration, and which has horizontal flat top and bottom surfaces, first and second thin flat nonwoven cloth pads of fused quartz fibers, both of which have flat upper and lower surfaces, the first of which pads is located on top of and in continuous intimate contact with the top surface of the silicon carbide ashing means, and the second of which pads is located atop the first pad, so that ashable material to be analyzed for ash content may be placed between such pads for such ashing to be effected, said second pad being permeable to passage of gas released during ashing of the ashable material and a refractory material in contact with the bottom surface of the ashing means so as to at least partially inhibit heat loss therefrom.

2. An apparatus according to claim 1 wherein the chamber is equipped with an exhaust fan to exhaust gases produced during ash analysis.

* * * * *